US008529480B2

(12) United States Patent
Dicerbo et al.

(10) Patent No.: US 8,529,480 B2

(45) Date of Patent: Sep. 10, 2013

(54) SYSTEM AND METHOD FOR TREATING CERVICAL VERTEBRAE

(76) Inventors: Mary T. M. Dicerbo, Barrington, IL (US); Bernard D. Asher, Barrington, IL (US)

( * ) Notice: Subject to any disclaimer, the term of this patent is extended or adjusted under 35 U.S.C. 154(b) by 820 days.

(21) Appl. No.: 12/435,478

(22) Filed: May 5, 2009

(65) Prior Publication Data

US 2009/0281570 A1 Nov. 12, 2009

Related U.S. Application Data

(60) Provisional application No. 61/050,780, filed on May 6, 2008.

(51) Int. Cl.
*A61F 5/00* (2006.01)

(52) U.S. Cl.
USPC ................................ 601/25; 601/24; 606/237

(58) Field of Classification Search
USPC .................. 601/5, 23, 24, 26, 33, 84, 85, 89, 601/90, 96, 97, 98, 25; 606/237, 240, 241, 606/243, 244, 245; 5/613, 622
See application file for complete search history.

(56) References Cited

U.S. PATENT DOCUMENTS

| | | | | |
|---|---|---|---|---|
| 4,960,111 | A | 10/1990 | Steffensmeier | |
| 5,320,640 | A | 6/1994 | Riddle et al. | |
| 5,320,641 | A * | 6/1994 | Riddle et al. .................. | 606/243 |
| 5,423,861 | A | 6/1995 | Kelley | |
| 6,436,126 | B1 | 8/2002 | McAfee | |
| 6,638,299 | B2 | 10/2003 | Cox | |
| 6,692,451 | B2 | 2/2004 | Splane, Jr. | |
| 6,749,548 | B2 | 6/2004 | Hoffman | |
| 6,971,997 | B1 | 12/2005 | Ryan et al. | |
| 2006/0047237 | A1 | 3/2006 | Pruett et al. | |

OTHER PUBLICATIONS

International Preliminary Report on Patentability and Written Opinion of the International Search Authority, International Application No. PCT/US2009/042836, International Filing Date: May 5, 2009, Applicant: DiCerbo, Mary, T., M. et al., mailed Nov. 18, 2010.

* cited by examiner

*Primary Examiner* — Quang D Thanh

(74) *Attorney, Agent, or Firm* — McAndrews, Held & Malloy, Ltd.

(57) ABSTRACT

Systems, methods and computer readable mediums encoded with computer instructions for treating cervical vertebrae are provided. Certain cervical vertebrae treatment devices include a head support configured to support a patient's head, and a motion component operably connected to the head support, wherein the motion component is configured to provide movement of the head support about at least three axes. Certain devices also include a control system operably connected to the motion component and configured to control operation of the motion component.

17 Claims, 13 Drawing Sheets

SYSTEM AND METHOD FOR TREATING CERVICAL VERTEBRAE

CROSS-REFERENCE TO RELATED APPLICATIONS/INCORPORATION BY REFERENCE

This application claims priority to U.S. Provisional Application No. 61/050,780 filed May 6, 2008, entitled "SYSTEM AND METHOD FOR TREATING CERVICAL VERTEBRAE," which application is incorporated by reference herein in its entirety.

BACKGROUND OF THE INVENTION

Embodiments of the present technology generally relate to systems and methods for treating cervical vertebrae.

Cervical vertebrae ailments can be painful and can limit an individual's daily activities. Further, if left untreated, cervical vertebrae ailments can lead to complications. For example, misaligned cervical vertebrae can lead to uneven pressure on discs, eventually leading to the nucleus pulposa creating pressure on annular fibers in one direction. Sustained pressure over time plus repetitive trauma of domestic activities in daily living or otherwise can lead to a risk of herniated discs. Chiropractic adjustments and cervical flexion-distraction can lead to centralization of nucleus, decrease wear and tear and aid realignment.

Devices configured to treat the cervical region and/or the lumbo/sacral region exist. See, for example, U.S. Patent Application Publication No. 2006/0047237, which names Pruett et al. and was published on Mar. 2, 2006; U.S. Pat. No. 6,692,451, which issued to Splane, Jr. on Feb. 17, 2004; U.S. Pat. No. 5,320,640, which issued to Riddle et al. on Jun. 14, 1994; and U.S. Pat. No. 4,960,111, which issued to Steffensmeier on Oct. 2, 1990.

However, known devices do not provide automated cervical flexion-distraction in desired ranges of motion. There is, therefore, a need for improved systems and methods for treating cervical vertebrae.

SUMMARY OF THE INVENTION

Certain embodiments provide systems, methods and computer readable mediums encoded with computer instructions for treating cervical vertebrae.

For example, in certain embodiments, a cervical vertebrae treatment device includes a head support configured to support a patient's head; and a motion component operably connected to the head support, wherein the motion component is configured to provide movement of the head support about at least three axes.

For example, in certain embodiments, a method for treating cervical vertebrae includes: providing a head support that is operably connected to a motion component configured to provide movement of the head support about at least three axes; and moving the head support using the motion component.

For example, in certain embodiments, a computer readable medium encoded with a set of computer instructions for treating cervical vertebrae includes: an input routine that allows at least one of patient information and treatment information to be input using a user interface; and a control routine that allows a computer processor to control operation of a motion component in a cervical vertebrae treatment device based on at least one of the patient information and the treatment information, wherein the motion component is configured to provide movement of a head support about at least three axes.

BRIEF DESCRIPTION OF THE DRAWING(S)

Figure 1:
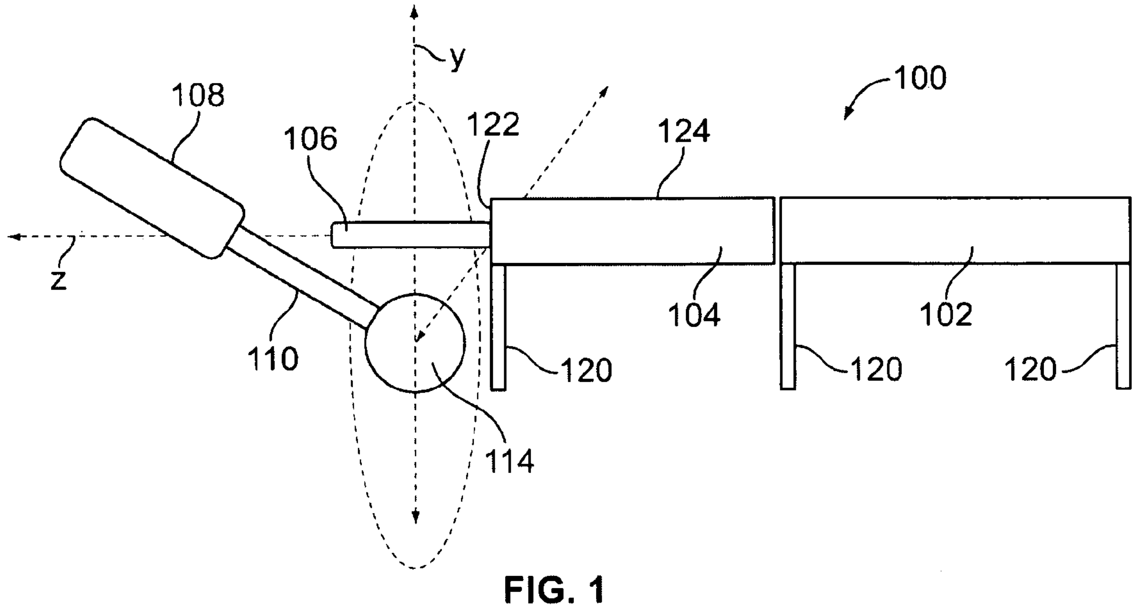
FIG. 1 illustrates a side view of a treatment device used in accordance with an embodiment of the present technology.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF PREFERRED EMBODIMENT(S)

Certain embodiments of the present technology provide systems and methods for treating cervical vertebrae. In the Figures, common elements are denoted with common identifiers.

FIG. 1 illustrates a side view of a treatment device 100 used in accordance with an embodiment of the present technology. The treatment device 100 includes: a lower table portion 102, a middle table portion 104, an upper table portion 106, legs 120, a head support 108, and a motion component 114 that includes an arm 110. The legs 120 are configured to maintain the lower table portion 102, middle table portion 104, and upper table portion 106 off the ground. In certain embodiments, for example, the table 100 may be raised or lowered to accommodate different size or disabled patients, for example, by adjusting the length of the legs 120. In certain embodiments, for example, the motion component 114 is disposed between one or more of the table portions and the ground. In certain embodiments, for example, the motion component is attached to one or more of the table portions using a fastening system that includes screws, bolts, and/or other fasteners. In certain embodiments, for example, the upper table portion 106 can be removable to accommodate different body sizes and shapes. The axis z indicates horizontal displacement relative to an end 122 of the middle table portion 104. The axis y indicates vertical displacement relative to a top 124 of the middle table portion 104. The arm 110 is attached to the head support 108. Movement of the arm 110 displaces the head support 108. In the embodiments described herein, for example, movement of the arm 110 can be achieved using the motion component 400 described in connection with FIGS. 4 and 5. In the embodiment shown in FIG. 1, for example, the motion component 114 is in communication with a control system, such as the control system described in connection with FIG. 23, for example, configured to control movement of the arm 110.

Figure 2:
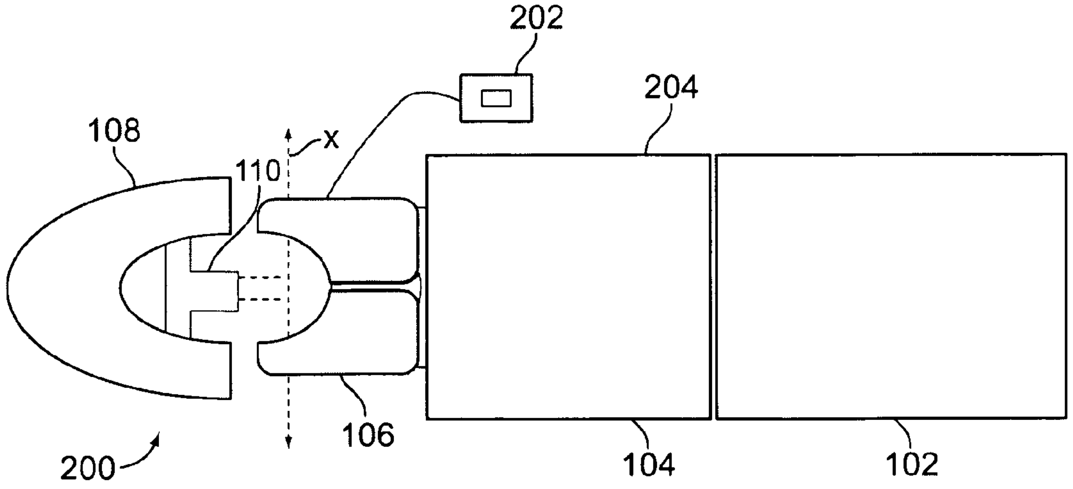
FIG. 2 illustrates a top view of a treatment device used in accordance with an embodiment of the present technology.

FIG. 2 illustrates a top view of a treatment device 200 used in accordance with an embodiment of the present technology. The axis x indicates horizontal displacement relative to a side 204 of the middle table portion 104. The treatment device 200 includes a switch 202 configured to deactivate the treatment device 200 such that the arm 110 does not move after the switch 202 is activated. In certain embodiments, for example, the switch 202 can be manually activated by depressing a button and/or voice-activated by speaking. In the embodiment shown in FIG. 2, for example, the switch 202 is in communication with a control system that can be configured to control the arm 110, such as the control system described in connection with FIG. 23, for example.

Figure 3:
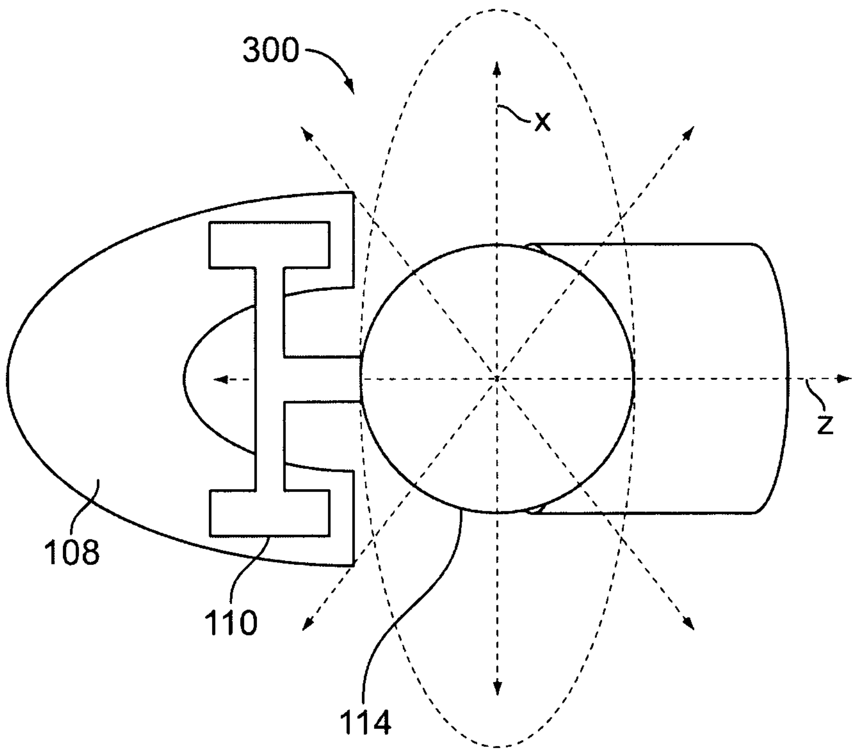
FIG. 3 illustrates a top view of components of a treatment device used in accordance with an embodiment of the present technology.

FIG. 3 illustrates a top view of components 300 of a treatment device used in accordance with an embodiment of the present technology. In FIG. 3, the head support 108 is transparent such that the components below are shown.

Figure 4:
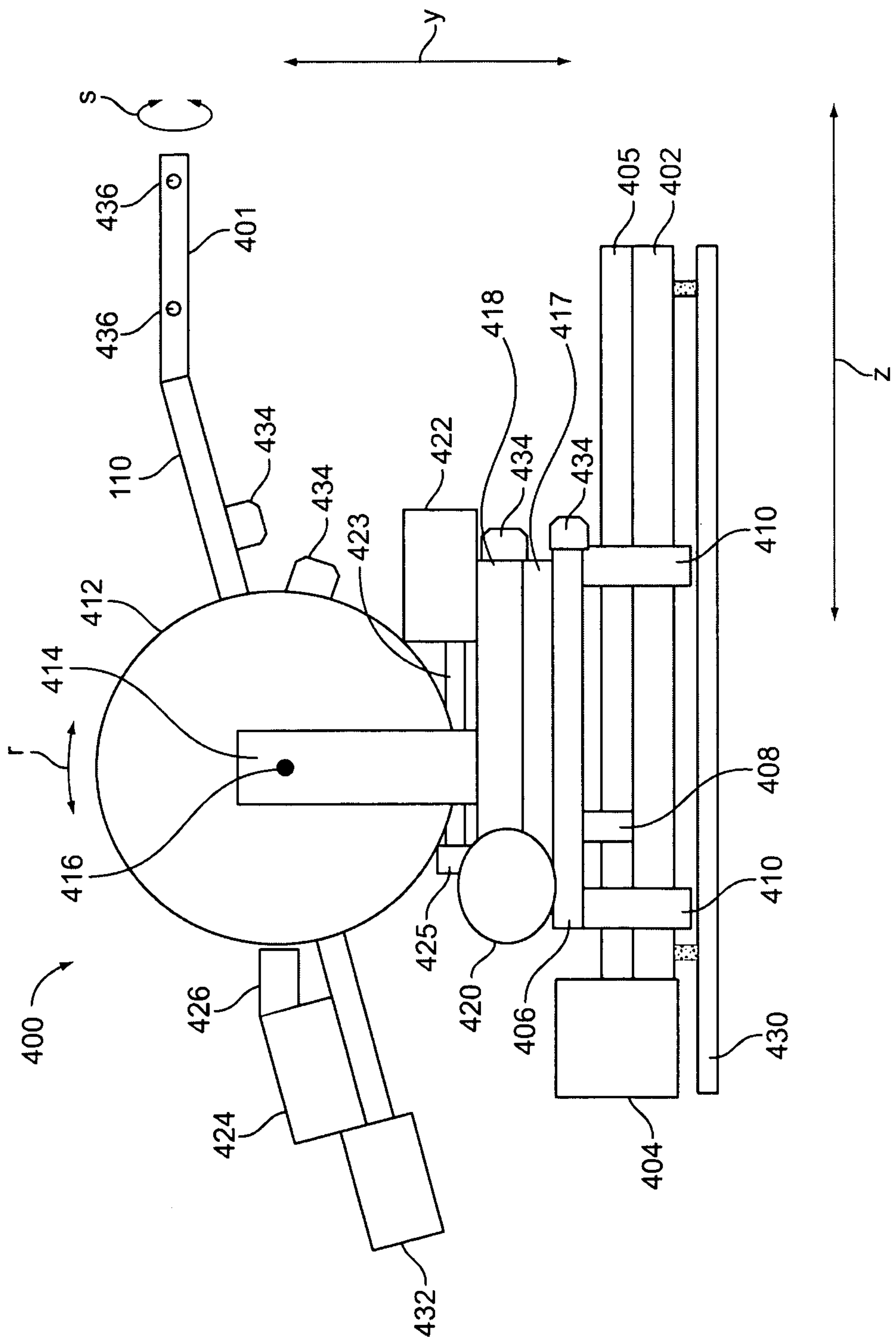
FIG. 4 illustrates a side view of a motion component of a treatment device used in accordance with an embodiment of the present technology.
Figure 5:
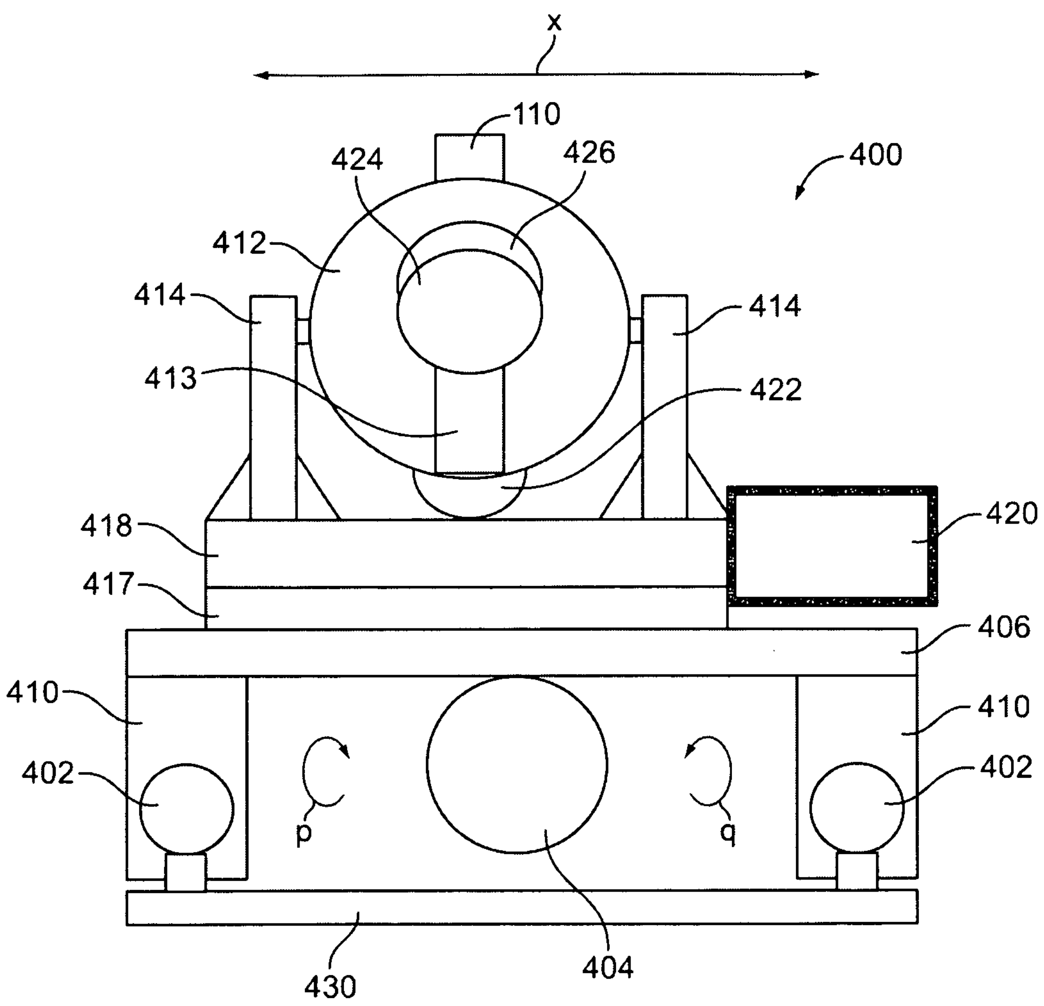
FIG. 5 illustrates a rear view of the motion component illustrated in FIG. 4.

FIG. 4 illustrates a side view of a motion component 400 of a treatment device used in accordance with an embodiment of the present technology. FIG. 5 illustrates a rear view of the motion component 400 illustrated in FIG. 4. The motion component 400 includes an arm 110 with a distal end 401 (shown in FIG. 4) to which a head support can be attached, for example, using holes 436. The motion component 400 can be used in connection with the treatment devices described in connection with FIGS. 1-3. The motion component 400 can be in communication with a control system, such as the control system described in connection with FIG. 23, for example, configured to control the motion component 400.

In the embodiment shown in FIGS. 4 and 5, for example, the motion component 400 includes guide rails 402, a first motor 404, a first motor screw 405, a cross support 406, a ball nut drive 408, tie rod supports 410, an arm support 412 with a threaded portion 413 provided therein, vertical supports 414, pins 416, a static plate 417, a rotating plate 418, a second motor 420, a third motor 422, a third motor screw 423, a third motor screw guide 425, an arm 110, a fourth motor 424, a fourth motor support 426, a mounting plate 430, a counter weight 432, and a plurality of position indicators 434.

In the embodiment shown in FIGS. 4 and 5, the motion component 400 includes a mounting plate 430 that can be fixedly attached to a treatment device, such as attached to an underside of a table portion and disposed beneath the table portion of the treatment device, for example. Fixedly attached to the mounting plate 430 are guide rails 402. The guide rails 402 are static and are in sliding engagement with the tie rod supports 410. The tie rod supports 410 are configured to slide over the guide rails 402 in the directions of the axis z. The cross support 406 is fixedly attached to the tie rod supports 410. The cross support 406 is also fixedly attached to the ball nut drive 408. The ball nut drive 408 includes a threaded interior cavity configured to receive the first motor screw 405. The first motor screw 405 is mounted with the first motor 404 and configured to rotate in a first direction p (shown in FIG. 5) and a second direction q (shown in FIG. 5). The second direction q is opposite the first direction p. Activating the first motor 404 can provide for rotation of the first motor screw 405 in the first direction p or the second direction q. Rotating the first motor screw 405 in the first direction p can cause displacement of the cross support 406 in a first direction of the axis z, and rotating the first motor screw 405 in the second direction q can cause displacement of the cross support 406 in the opposite direction of the axis z. Displacement of the cross support 406 in either direction of the axis z likewise causes the arm 110 to be displaced in such direction of the axis z. Movement of the arm 110 in a direction of the axis z can provide for adjustment of a treatment device to fit a patient, for example, based on the height and/or body type of the patient. In certain embodiments, for example, the arm 110 can be displaced in a direction of the axis z up to 6 inches. Once a desired position about the z-axis is identified, the position of the arm 110 can be fixed in regard to the z-axis such that the arm 110 (and the head support 108 attached to the arm 110) cannot be displaced in a direction of the axis z. In certain applications, displacement of the arm 110 in a direction of the axis z may not be desired.

In the embodiment shown in FIGS. 4 and 5, for example, the static plate 417 is fixedly attached to the cross support 406. The static plate 417 is attached to the rotating plate 418 such that the lower surface of the rotating plate 418 can rotate about the upper surface of the static plate 417. The rotating plate 418 is mounted with the second motor 420 and configured to rotate in a first direction and the opposite direction about the upper surface of the static plate 417. Activating the second motor 420 can provide for rotation of the rotating plate 418 in the first direction or the opposite direction. Rotating the rotating plate 418 in the first direction can cause displacement of the arm 110 in a first direction of the axis x (shown in FIG. 5), and rotating the rotating plate 418 in the opposite direction can cause displacement of the arm 110 in the opposite direction of the axis x. In certain embodiments, for example, the arm 110 can be displaced in a direction of the axis x up to 120 degrees. The position of the arm 110 can be fixed in regard to the x-axis such that the arm 110 (and the head support 108 attached to the arm 110) cannot be displaced in a direction of the axis x. In certain applications, displacement of the arm 110 in a direction of the axis x may not be desired.

In the embodiment shown in FIGS. 4 and 5, for example, the vertical supports 414 are fixedly attached to the rotating plate 418. The vertical supports 414 are attached to pins 416 that engage the arm support 412. The arm support 412 is configured to rotate about the pins 416 in the directions of the radius r. The arm support 412 shown in FIGS. 4 and 5 is spherical. In other embodiments, for example, the arm support is not spherical, for example, the arm support can be cylindrical with the flat portions engaging the pins. The arm support 412 includes a threaded portion 413 configured to receive the third motor screw 423. The third motor screw 423 is mounted with the third motor 422 and configured to rotate in a first direction p (shown in FIG. 5) and a second direction q (shown in FIG. 5). The second direction q is opposite the first direction p. Activating the third motor 422 can provide for rotation of the third motor screw 423 in the first direction p or the second direction q. Rotating the third motor screw 423 in the first direction p can cause rotation of the arm support 412 in a first direction of the radius r about the pins 416, thereby causing displacement of the arm 110 in a first direction of the axis y. Rotating the third motor screw 423 in the second direction q can cause rotation of the arm support 412 in the opposite direction of the radius r about the pins 416, thereby causing displacement of the arm 110 in the opposite direction of the axis y. In certain embodiments, for example, the arm 110 can be displaced in a direction of the axis y up to 130 degrees. The position of the arm 110 can be fixed in regard to the y-axis such that the arm 110 (and the head support 108 attached to the arm 110) cannot be displaced in a direction of the axis y. In certain applications, displacement of the arm 110 in a direction of the axis y may not be desired.

In the embodiment shown in FIGS. 4 and 5, for example, the fourth motor 424 and the fourth motor support 426 are mounted with the arm support 412. The fourth motor 424 engages the arm 110 such that activation of the fourth motor 424 can rotate the arm 110 in a first direction or the opposite direction indicated by s. In certain embodiments, for example, the arm 110 can be rotated in a direction of the radius s up to 90 degrees. In certain embodiments, for example, a counter weight 432, such as an eleven pound counter weight, for example, can be attached to the fourth motor 424.

In the embodiment shown in FIGS. 4 and 5, for example, indicators 434 disposed on the arm 110, arm support 412, rotating plate 418 and the cross support 406 can be used to indicate the respective positions of the arm 110, arm support 412, rotating plate 418 and the cross support 406.

In certain embodiments, for example, the fourth motor 424 or a fifth motor (not shown) can activate a system configured to pivot the head support 108 about the arm 110. Pivoting of a head support 108 about the arm 110 is shown, for example, in FIG. 12.

Figure 5A:
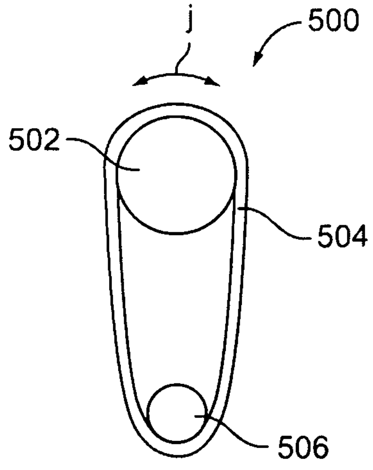
FIG. 5A illustrates a top view of components of a treatment device used in accordance with an embodiment of the present technology.
Figure 12:
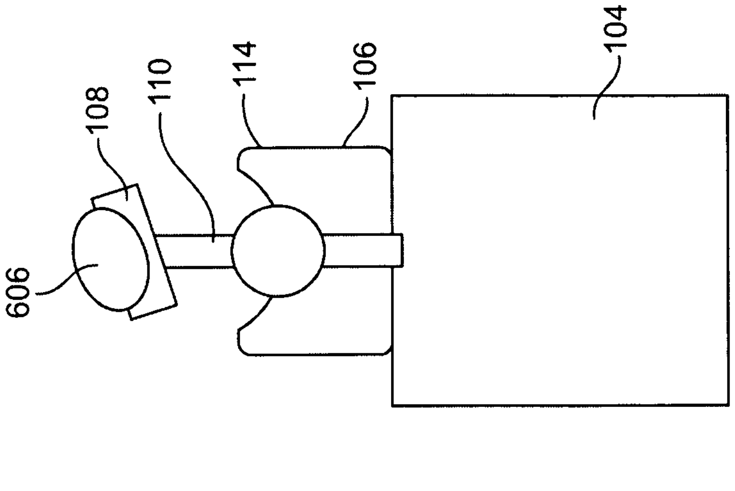
FIG. 12 illustrates a top view of the treatment device illustrated in FIG. 11.

FIG. 5A illustrates a system 500 configured to pivot the head support 108 about the arm. The system includes a first gear 502, a translational member 504, and a second gear 506. In certain embodiments, for example, the head support 108 can be attached to the first gear 502 such that rotation of the first gear 502 pivots the head support 108 as shown in FIG. 12, for example. The first gear 502 is connected to the second gear 506 via the translational member 504 such that rotation of the second gear 506 in a first direction of the radius j rotates the first gear 502 in the first direction, thereby pivoting a connected head support 108 in the first direction. Likewise, rotation of the second gear 506 in a second direction opposite the first direction rotates the first gear 502 in the second direction, thereby pivoting a connected head support 108 in the second direction.

In certain embodiments, for example, the fourth motor 424 described in connection with FIGS. 4 and 5 can activate the system 500 by rotating the second gear 506. In certain embodiments, for example, a fifth motor can activate the system 500 by rotating the second gear 506. In certain embodiments, for example, the system 500 can be mounted within the arm 110 described in connection with FIGS. 4 and 5.

Figure 6:
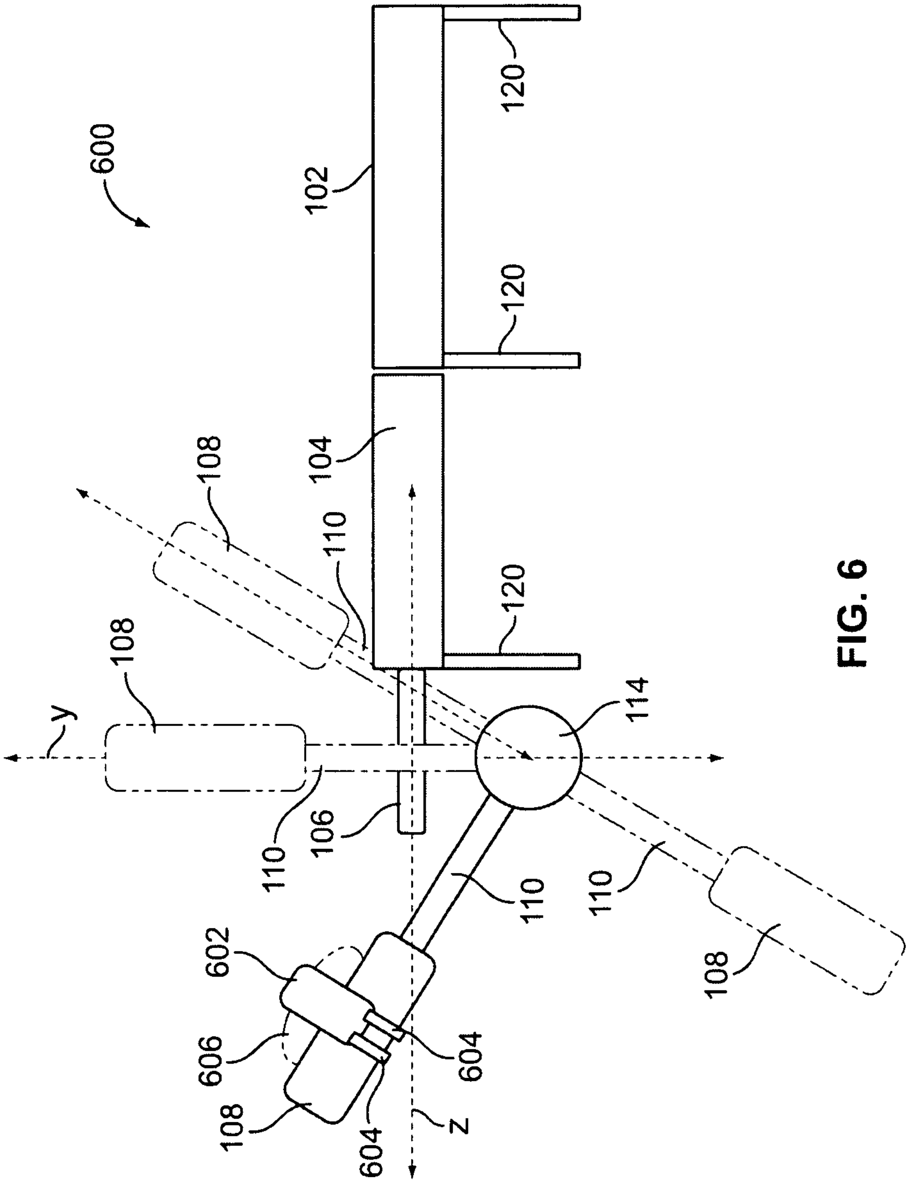
FIG. 6 illustrates a side view of a treatment device used in accordance with an embodiment of the present technology.

FIG. 6 illustrates a side view of a treatment device 600 used in accordance with an embodiment of the present technology. FIG. 6 illustrates movement of the head support 108 between a plurality of positions. The treatment device 600 includes a brace 602 that includes straps 604. The straps 604 are configured to be secured to the head support 108, thereby securing a patient's head 606 to the head support 108. The brace 602 is configured such that a patient's face would be directed toward the head support 108 and the brace 602 wraps around the back of the patient's head 606. In certain embodiments, for example, the straps 604 and the head support 108 can include Velcro to secure the straps 604 to the head support 108.

Figure 7:
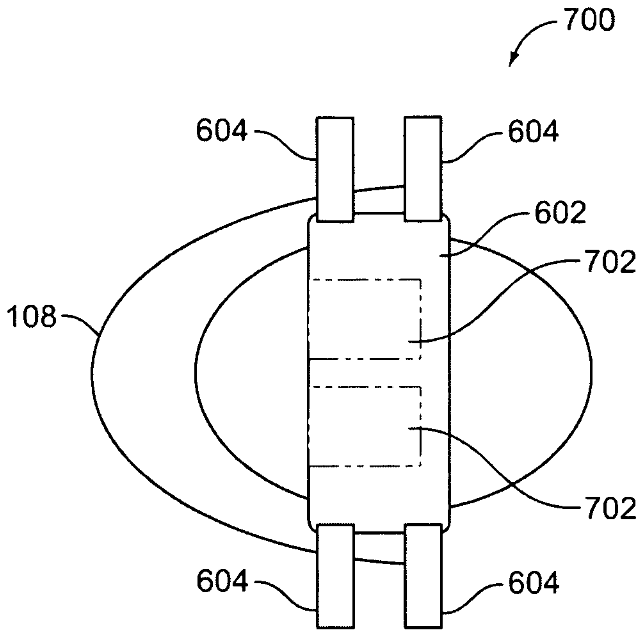
FIG. 7 illustrates a top view of components of a treatment device used in accordance with an embodiment of the present technology.
Figure 8:
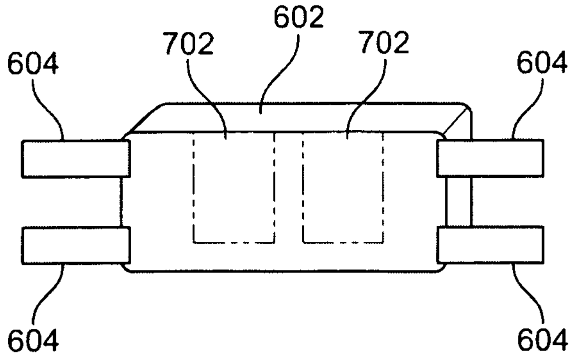
FIG. 8 illustrates a perspective view of a component of a treatment device used in accordance with an embodiment of the present technology.
Figure 9:
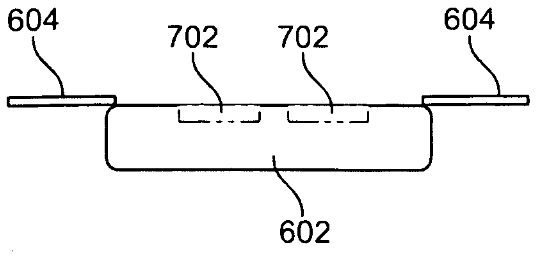
FIG. 9 illustrates a side-sectional view of a component of a treatment device used in accordance with an embodiment of the present technology.

FIG. 7 illustrates a top view of components 700 of a treatment device used in accordance with an embodiment of the present technology. In the embodiment shown in FIG. 7, for example, the brace 602 includes a plurality of weights 702, such as sand bags, for example, that can provide pressure to the back of a patient's head, thereby securing the patient's head to the head support 108. FIG. 8 illustrates a perspective view of the brace 602 described in connection with FIG. 7. FIG. 9 illustrates a side-sectional view of the brace 602 described in connection with FIGS. 7 and 8. In certain embodiments, for example, a brace can be figured similarly to the brace 602 but without including the weights 702.

In the embodiments described in connection with FIGS. 6-9, the patient's face is directed toward the head support 108 and the brace 602 wraps around the back of the patient's head 606. In other embodiments, for example, the patient's face is directed away from the head support 108 and a brace can include a chin strap and/or a forehead strap.

Figure 10:
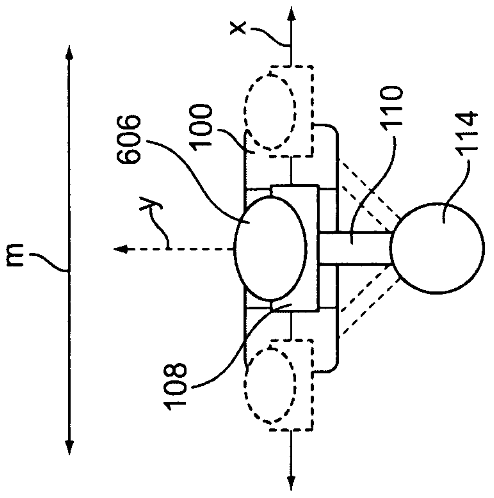
FIG. 10 illustrates a front-end view of components of a treatment device used in accordance with an embodiment of the present technology.

FIG. 10 illustrates a front-end view of components of a treatment device used in accordance with an embodiment of the present technology. FIG. 10 illustrates an exercise that comprises side-to-side movement of the head support 108, which results in lateral flexion of the head 606 in the plane horizontal to the table 100. The movement of the head support 108 and the head 606 is indicated by m. If viewed from above, the head support 108 moves in an arcing motion due to the constant length of the arm 110. This motion can be achieved using the motion component 400 (described in connection with FIGS. 4 and 5) by activating the second motor 420 to provide horizontal displacement of the arm 110 in the directions of the axis x.

Figure 11:
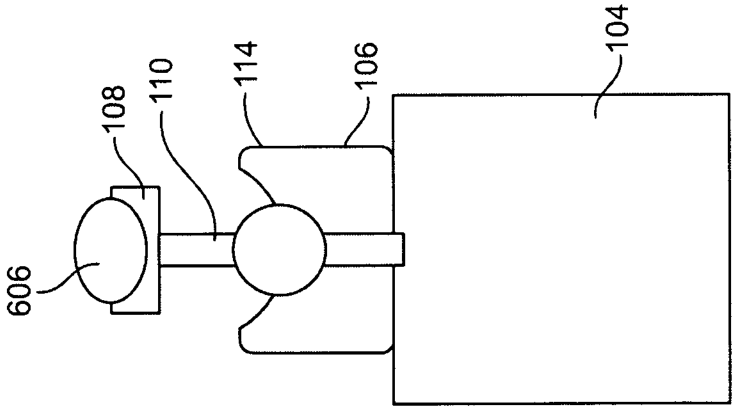
FIG. 11 illustrates a top view of a treatment device used in accordance with an embodiment of the present technology.

FIGS. 11 and 12 illustrate top views of components of a treatment device used in accordance with an embodiment of the present technology. In FIG. 12, the head support 108 is pivoted about the arm 110. In certain embodiments, for example, exercises can be implemented with the head support pivoted 15-30 degrees to the left or right from the normal position (shown in FIG. 11). Pivoting of the head support 108 about the arm 110 can be achieved using the motion component 400 (described in connection with FIGS. 4 and 5) by activating the fourth motor 422 and/or a fifth motor to activate the system 500 (described in connection with FIG. 5A) configured to pivot the head support 108 about the arm 110.

Figure 13:
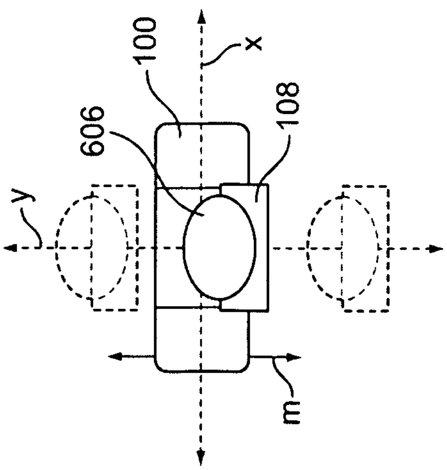
FIG. 13 illustrates a front-end view of components of a treatment device used in accordance with an embodiment of the present technology.
Figure 16:
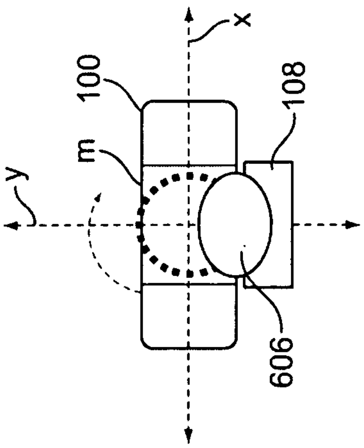
FIG. 16 illustrates a front-end view of components of a treatment device used in accordance with an embodiment of the present technology.
Figure 17:
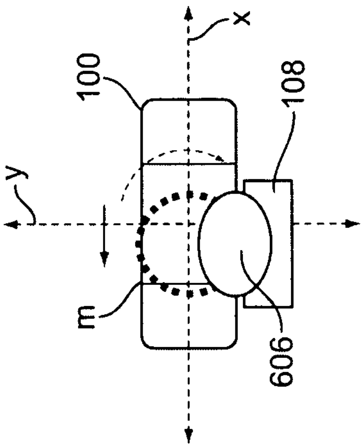
FIG. 17 illustrates a front-end view of components of a treatment device used in accordance with an embodiment of the present technology.
Figure 18:
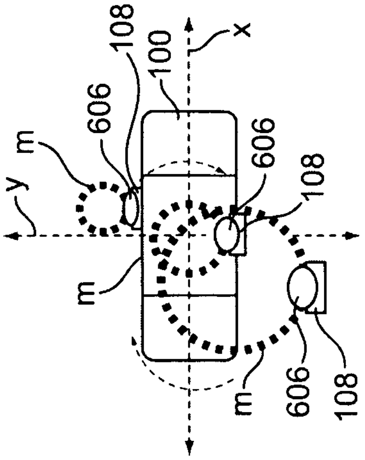
FIG. 18 illustrates a front-end view of components of a treatment device used in accordance with an embodiment of the present technology.
Figure 19:
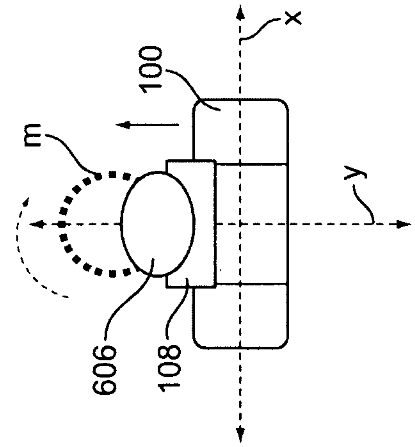
FIG. 19 illustrates a front-end view of components of a treatment device used in accordance with an embodiment of the present technology.
Figure 20:
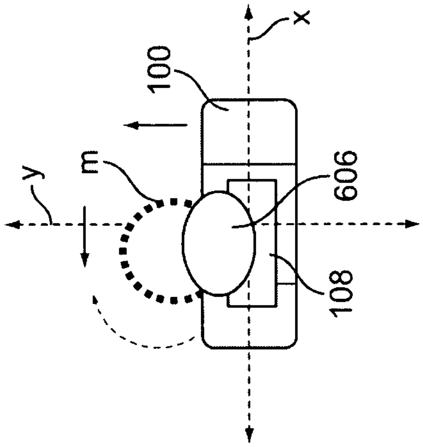
FIG. 20 illustrates a front-end view of components of a treatment device used in accordance with an embodiment of the present technology.
Figure 20A:
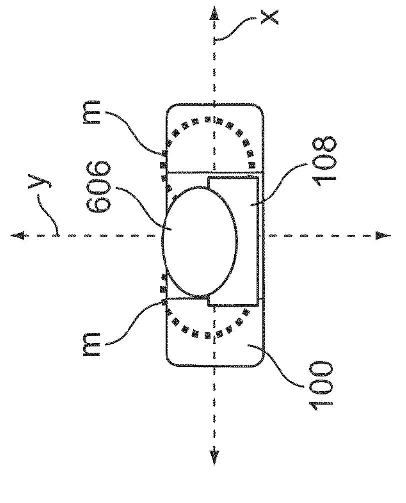
FIG. 20A illustrates a front-end view of components of a treatment device used in accordance with an embodiment of the present technology.
Figure 20B:
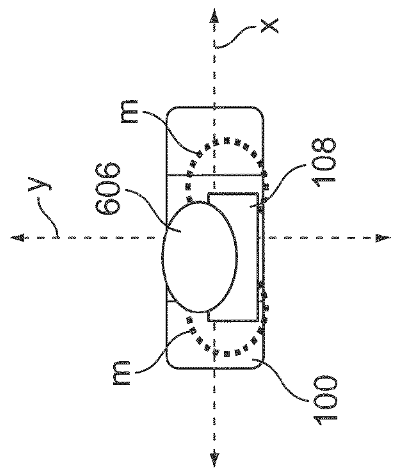
FIG. 20B illustrates a front-end view of components of a treatment device used in accordance with an embodiment of the present technology.
Figure 20C:
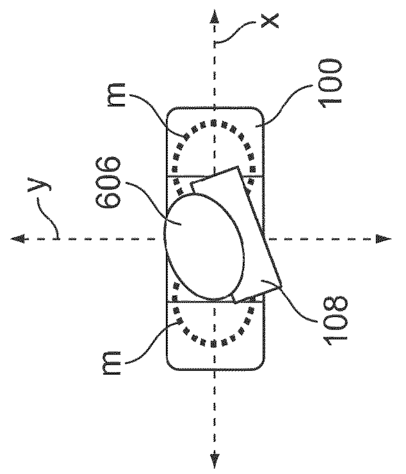
FIG. 20C illustrates a front-end view of components of a treatment device used in accordance with an embodiment of the present technology.
Figure 20D:
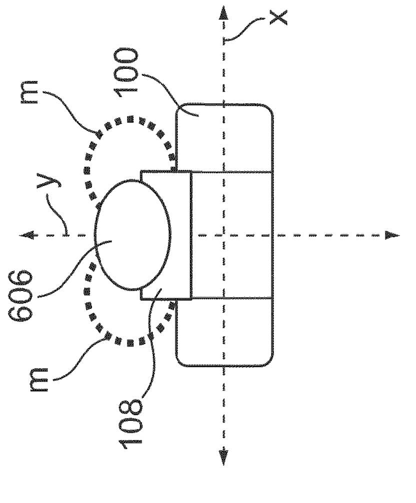
FIG. 20D illustrates a front-end view of components of a treatment device used in accordance with an embodiment of the present technology.
Figure 20E:
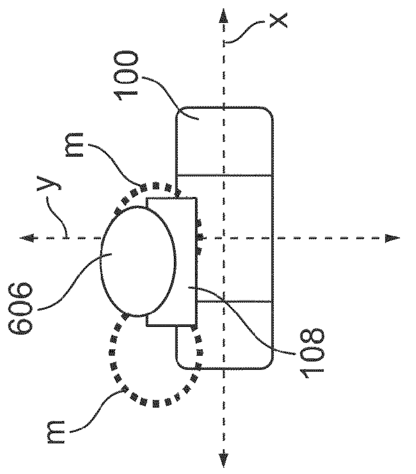
FIG. 20E illustrates a front-end view of components of a treatment device used in accordance with an embodiment of the present technology.
Figure 20F:
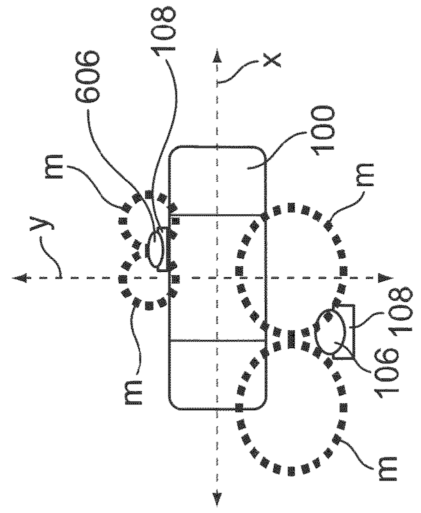
FIG. 20F illustrates a front-end view of components of a treatment device used in accordance with an embodiment of the present technology.

FIG. 13 illustrates a front-end view of components of a treatment device used in accordance with an embodiment of the present technology. FIG. 13 illustrates up and down movement of the head support 108, which results in vertical flexion of the head 606 in the plane vertical to the table 100. The movement of the head support 108 and the head 606 is indicated by m. If viewed from the side, the head support 108 moves in an arcing motion due to the constant length of the arm 110. This motion can be achieved using the motion component 400 (described in connection with FIGS. 4 and 5) by activating the third motor 422 to provide vertical displacement of the arm 110 in the directions of the axis y.

Figure 15:
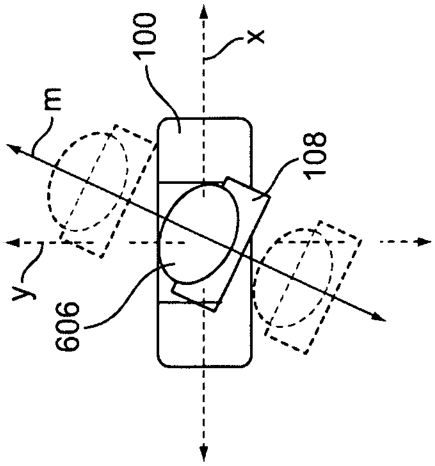
FIG. 15 illustrates a front-end view of components of a treatment device used in accordance with an embodiment of the present technology.
Figure 14:
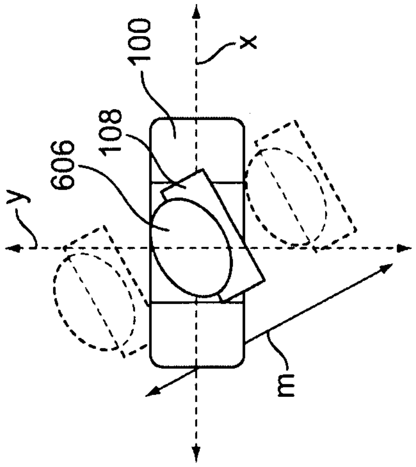
FIG. 14 illustrates a front-end view of components of a treatment device used in accordance with an embodiment of the present technology.

FIGS. 14 and 15 illustrate front-end views of components of a treatment device used in accordance with an embodiment of the present technology. FIGS. 14 and 15 illustrate up and down movement of the head support 108 in a tilted position, which results in flexion of the head 606 in both vertical and horizontal planes to the table 100. In certain embodiments, for example, the head support can be tilted about 15-45 degrees from the position shown in FIG. 13. The movement of the head support 108 and the head 606 is indicated by m. If viewed from the side or above, the head support 108 moves in an arcing motion due to the constant length of the arm 110. This motion can be achieved using the motion component 400 (described in connection with FIGS. 4 and 5) by first activating the fourth motor 424 to provide rotation of the arm 110 in a direction of the radius s, and then activating the second motor 420 and the third motor 422 to provide simultaneous horizontal and vertical displacement of the arm 110.

FIGS. 16-20F illustrate front-end views of components of a treatment device used in accordance with an embodiment of the present technology. FIGS. 16-20 illustrate circumduction of the head support 108 relative to the table 100, which results in circumduction of the head 606. FIGS. 20A-20F illustrate saccro-occipital (SOT) motion of the head support 108 relative to the table 100, which results in SOT motion of the head 606. In FIGS. 16-20F, the movement of the head support 108 and the head 606 is indicated by m. If viewed from the side or above, the head support 108 moves in an arcing motion due to the constant length of the arm 110. This motion can be achieved using the motion component 400 (described in connection with FIGS. 4 and 5) activating the second motor 420 and the third motor 422 to provide simultaneous horizontal and vertical displacement of the arm 110.

In connection with the exercises described in connection with FIGS. 10 and 13-20F, each exercise can be started from a normal position, wherein the patient's head is not displaced vertically or horizontally. Exercises can also be started from a position that is offset horizontally and/or vertically from such a normal position. Normal positions and/or offset positions can be identified using indicators 434. In certain embodiments, for example, exercises can be started from a position that is offset horizontally and/or vertically 15-30 degrees from the normal position. Also, the radius of circumduction and/or SOT motion can be varied between different exercises and/or within an exercise. An exercise can include any number of repetitions, and preferably includes 1-20 repetitions. In certain embodiments, for example, an exercise can be implemented at a low rate of speed, or a higher rate of speed. In certain embodiments, for example, an exercise can be implemented at a constant rate of speed or a varying rate of speed. In certain embodiments, for example, an exercise can be implemented at a low torque, or a higher torque. In certain embodiments, for example, an exercise can be implemented at a constant torque or a varying torque. In certain embodiments, for example, certain positions of an exercise, for example, a fully extended position, can be held for a certain amount of time, for example, 10-20 seconds.

Figure 21:
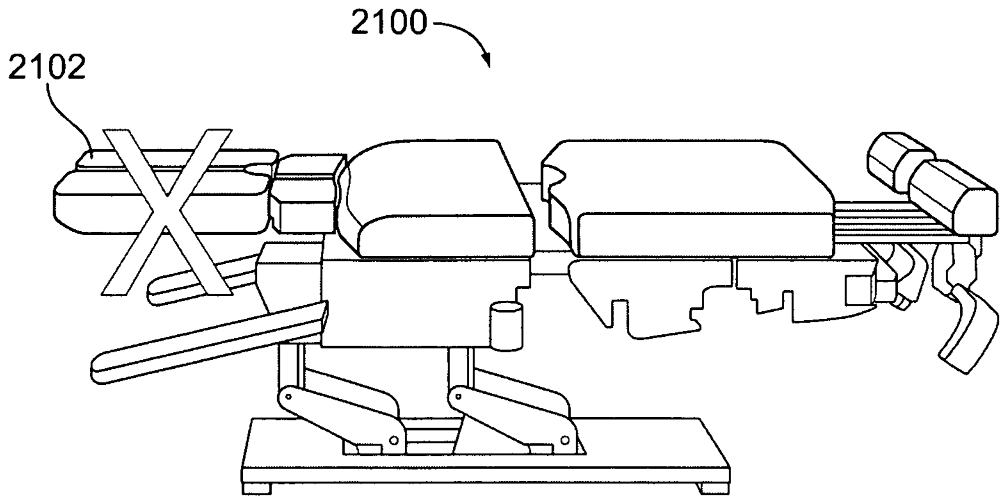
FIG. 21 is a perspective view of a prior art treatment device.
Figure 22:
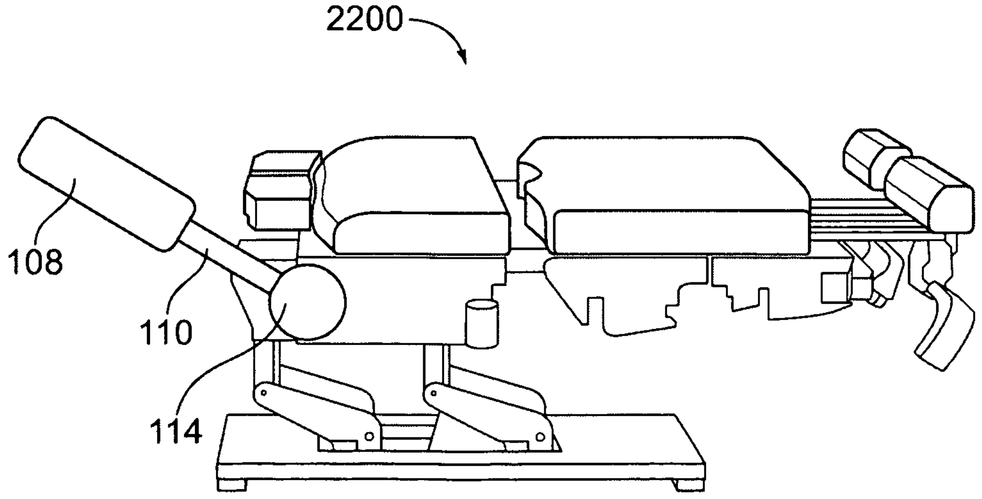
FIG. 22 illustrates a modified treatment device 2200 that includes components used in accordance with an embodiment of the present technology.

FIG. 21 is a perspective view of a prior art treatment device 2100. The prior art treatment device includes a head support 2102 that is not capable of the range of motion of devices used in accordance with embodiments of the present technology. FIG. 22 illustrates a modified treatment device 2200 that includes components used in accordance with an embodiment of the present technology. Specifically, the modified device 2200 includes a motion component 114, arm 110 and head support 108 configured to provide the range of motion described in connection with FIGS. 1-20. In certain embodiments, an existing table can be modified/retrofitted by attaching a motion component 114, arm 110 and head support 108 configured to provide the range of motion described in connection with FIGS. 1-20.

Figure 23:
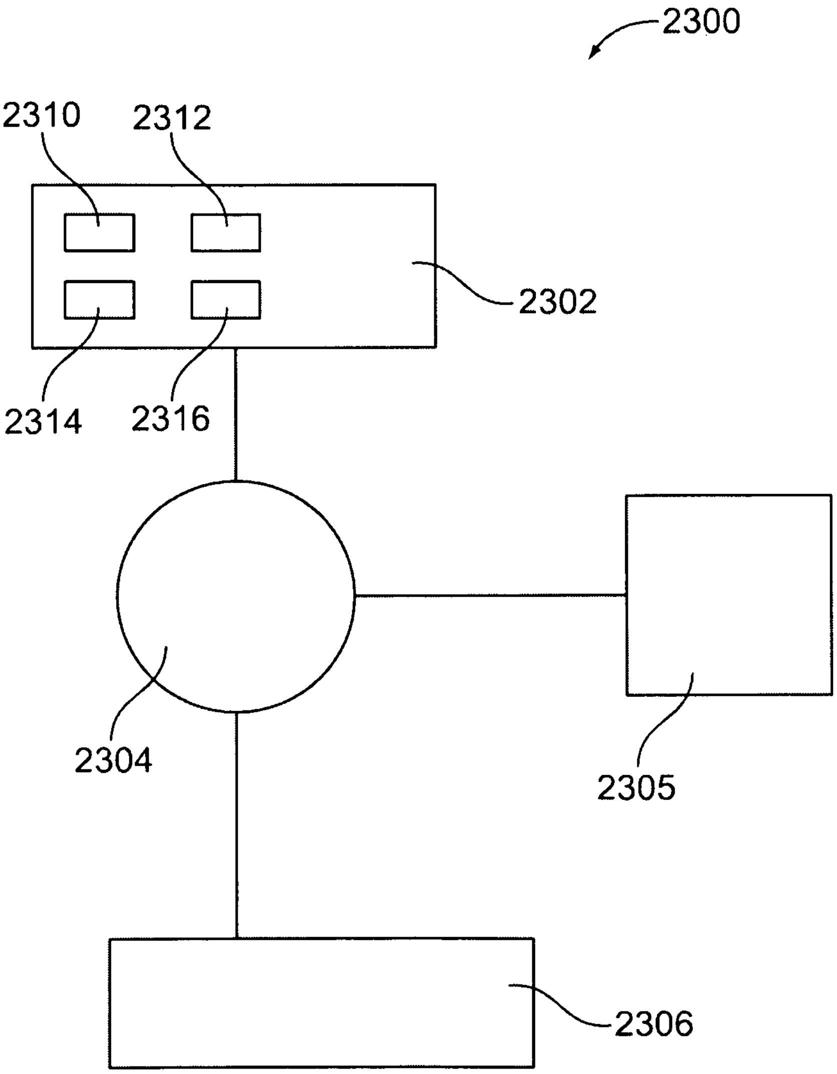
FIG. 23 illustrates a control system used in accordance with an embodiment of the present technology.

FIG. 23 illustrates a control system 2300 used in accordance with an embodiment of the present technology. The control system 2300 includes an input module 2302, a processor 2304, a memory 2305, and an output module 2306. The input module 2302 is configured to receive information from a user (for example, patient and/or a caregiver). The memory 2305 is configured to store information that can be accessed by the processor 2304, such as in a database of patient histories, for example. The output module 2306 is configured to output information. In certain embodiments, for example, the input module 2302, processor 2304, memory 2305 and output module 2306 can be implemented in hardware, firmware and/or software and can be implemented separately and/or integrated in various combinations.

In certain embodiments, for example, the input module 2302 can be configured to receive information via a graphical user interface 2310, a keyboard 2312, a switch integrated with a treatment device 2314 and/or a microphone 2316. For example, in certain embodiments, a caregiver can enter information regarding an exercise sequence via a graphical user interface and/or a keyboard. For example, the caregiver can select from exercise options that include vertical flexion, lateral flexion, stretching/extension, circumduction, sacro-occipital (SOT) motion and/or face pad rotation. Each exercise can be optionally customized as to the number of repetitions of the exercise, the range of motion of the exercise, the speed at which the exercise is carried out and/or the torque that will be applied. An exercise sequence can be optionally customized to include any number of exercises and/or repetition of exercises. For example, in certain embodiments, an exercise sequence can include 15 exercises and 30 repetitions.

In certain embodiments, for example, exercise sequences and/or individual exercises can be saved in memory 2305, in a database, for example, such that previously programmed sequences and/or individual exercises are accessible for modification and/or implementation. Such a database can include, for example, fields for the: patient, exercise, number of repetitions of an exercise, range of motion of an exercise, speed of an exercise, and/or torque of an exercise.

In certain embodiments, for example, completion of an exercise sequence can be saved in memory 2305, in a database, for example, such that completed exercise sequences are accessible for statistical and/or patient-based reporting. Such a database can include, for example, fields for the: patient, exercise, number of repetitions of an exercise, range of motion of an exercise, speed of an exercise, and/or torque of an exercise.

Once an exercise sequence is created, it can be implemented via a treatment device that is operably connected to and controlled by the processor 2304. Examples of such treatment devices are shown and described in connection with FIGS. 1-20F and 22. In certain embodiments, for example, a single run-through of an exercise sequence that includes multiple repetitions can be implemented. Such a run-through can allow a caregiver to validate the exercise sequence and/or allow a patient to communicate any pain that may result from implementing the exercise sequence. After such a run-through, the full exercise sequence can be implemented.

In certain embodiments, for example, an exercise sequence can be stopped by a patient and/or caregiver by manually activating the switch 2314 and/or by voice-activation via the microphone 2316. In certain embodiments, for example, an exercise sequence can be stopped by a caregiver via the graphical user interface 2310 and/or the keyboard 2312.

In certain embodiments, for example, the output module 2306 can be configured to output information as a visual display and/or printed matter. Information that can be output via the output module includes, for example: programming information (for use when selecting and/or modifying an exercise sequence), status information (for use during exercise sequence implementation) and reporting information (for providing details of completed sequences).

Figure 24:
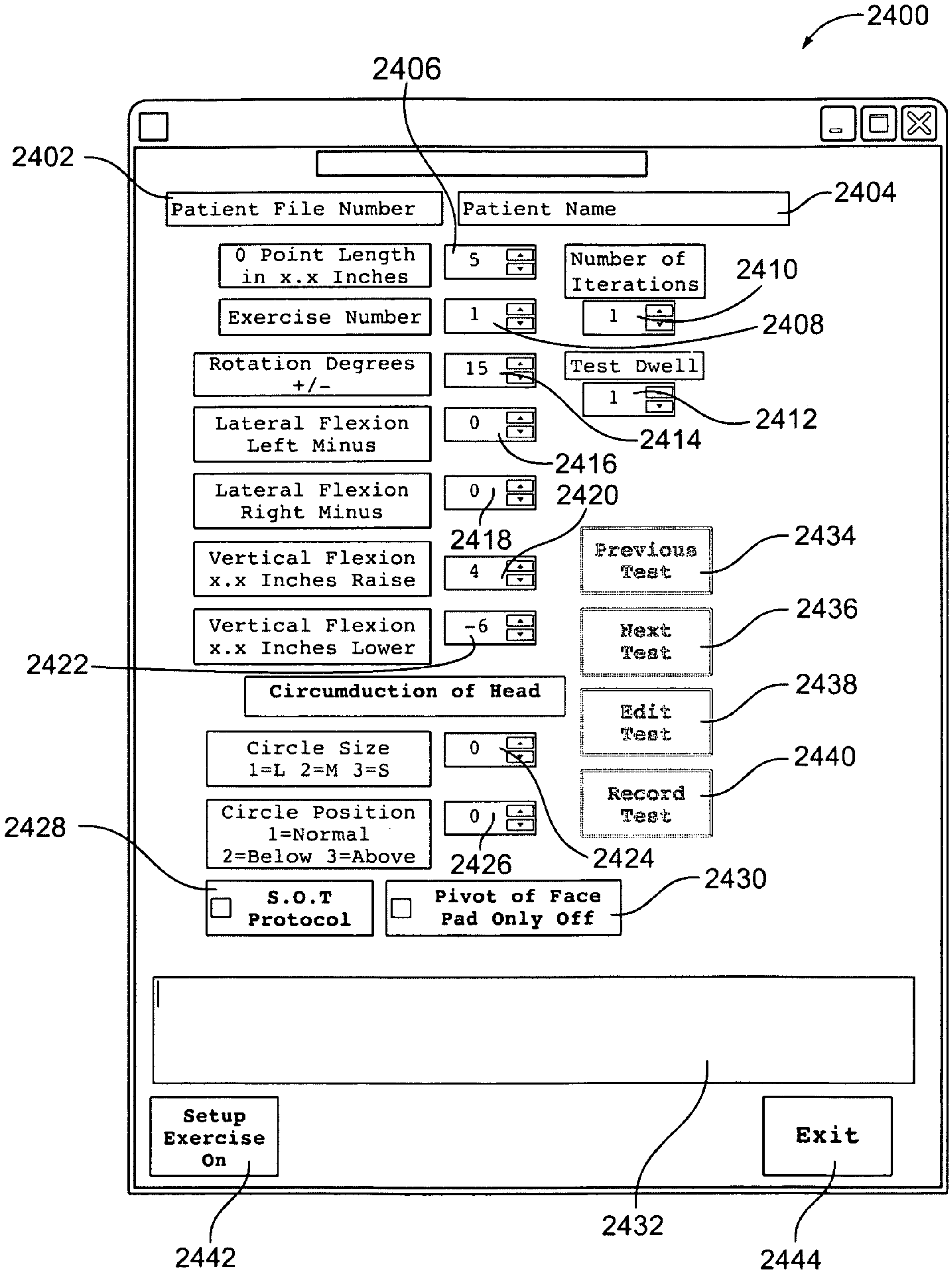
FIG. 24 illustrates a dialog for a user-interface used in accordance with an embodiment of the present technology.

FIG. 24 illustrates a dialog 2400 for a user-interface used in accordance with an embodiment of the present technology. The dialog 2400 includes fields configured such that patient information and exercise information can be input and/or edited. The dialog 2400 can be operably connected with the control system described in connection with FIG. 23. For example, in certain embodiments, the dialog 2400 can be operably connected with the input module described in connection with FIG. 23.

The dialog 2400 includes a field 2402 in which patient identification information, such as a patient file number, for example, can be entered. The dialog 2400 includes a field 2404 in which a patient's name can be entered. The dialog 2400 includes a field 2432 in which notes can be entered. The dialog 2400 includes a field 2408 in which an exercise identification number can be entered. The dialog 2400 includes a field 2410 in which the number of times an exercise is to be iterated can be entered.

The dialog 2400 includes a field 2406 in which a length can be entered that corresponds to displacement in the direction of the axis z as shown and described in connection with FIGS. 4 and 5. The dialog 2400 includes a field 2414 in which a degree of rotation can be entered that corresponds to rotation about the radius s as shown and described in connection with FIGS. 4 and 5.

The dialog 2400 includes a field 2416 in which lateral flexion in a first direction (e.g., to the left) can be entered that corresponds to displacement in the direction of the axis x as shown and described in connection with FIGS. 4 and 5. The dialog 2400 includes a field 2418 in which lateral flexion in a second direction that is opposite of the first direction (e.g., to the right) can be entered that corresponds to displacement in the direction of the axis x as shown and described in connection with FIGS. 4 and 5.

The dialog 2400 includes a field 2420 in which vertical flexion in a first direction (e.g., up) can be entered that corresponds to displacement in the direction of the axis y as shown and described in connection with FIGS. 4 and 5. The dialog 2400 includes a field 2422 in which lateral flexion in a second direction that is opposite of the first direction (e.g., down) can be entered that corresponds to displacement in the direction of the axis y as shown and described in connection with FIGS. 4 and 5.

The dialog 2400 includes a field 2424 in which circumduction size information can be entered. In certain embodiments, for example, entering circumduction size information can include choosing a predetermined circle size using corresponding identifiers. In such embodiments, 1 can be entered to indicate circumduction in a large radius; 2 can be entered to indicate circumduction in a medium radius; and 3 can be entered to indicate circumduction in a small radius. In certain embodiments, for example, entering circumduction size information can include entering the actual circle radius to be used in circumduction.

The dialog 2400 includes a field 2426 in which circumduction position information can be entered. In certain embodiments, for example, entering circumduction position information can include choosing a predetermined circle position using corresponding identifiers. In such embodiments, for example, 1 can be entered to indicate circumduction in the normal position (i.e., circumduction about a set point with no lateral or vertical offsets); 2 can be entered to indicate circumduction in a lowered position (i.e., circumduction about a set point that is vertically offset below the normal position without being laterally offset); 3 can be entered to indicate circumduction in a raised position (i.e., circumduction about a set point that is vertically offset above the normal position without being laterally offset). In certain embodiments, for example, entering circumduction position information can include entering the actual distance to be offset from the normal position in a vertical and/or lateral direction.

The dialog 2400 includes a field 2428 in which SOT motion can be indicated. Indicating SOT motion can provide for SOT motion as shown in FIGS. 20A-20F. In such embodiments, for example, the circumduction size and circumduction position information can be used to provide for the size and positioning of the SOT motion.

The dialog 2400 includes a field 2430 in which head support pivot information can be entered that corresponds to pivoting of the head support as shown and described in connection with FIG. 12, for example. In certain embodiments, for example, a dialog can the left) can be entered. In certain embodiments, for example, a dialog can include a field in which the degree of pivot in a second direction that is opposite of the first direction (e.g., to the right) can be entered.

The dialog 2400 includes a previous button 2434 that when activated can move to an exercise that precedes the current exercise based on exercise number. The dialog 2400 includes a next button 2436 that when activated can move to an exercise subsequent to the current exercise based on exercise number. The dialog 2400 includes an edit button 2438 that when activated can allow the fields of the current exercise to be edited. The dialog 2400 includes a record button 2440 that when activated can allow the fields of the current exercise to be saved. The dialog 2400 includes a setup button 2442 that when activated can allow the exercise sequence to be saved. The dialog 2400 includes an exit button 2444 that when activated exits the dialog.

In certain embodiments, for example, a dialog for a user-interface used in accordance with an embodiment of the present technology, does not include all of the fields shown in FIG. 24. In certain embodiments, for example, a dialog for a user-interface used in accordance with an embodiment of the present technology, can include fields not shown in FIG. 24.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A cervical vertebrae treatment device including:

a head support configured to support a patient's head; and a motion component operably connected to the head support, wherein the motion component comprises:

an arm operably connected to the head support;

a mounting plate;

a base plate rotatably connected to the mounting plate;

an arm support rotatably connected to the base plate;

a first motor mounted to the arm support and operably engaged with the arm to rotate the arm with respect to the arm support about a first longitudinal axis of the arm;

a second motor connected to the base plate and operably engaged with the arm support to rotate the arm support and the arm with respect to the base plate such that the arm can be displaced in a vertical direction along a second axis; and a third motor connected to the mounting plate and operably engaged with the base plate to rotate the base plate, the arm support and the arm with respect to the mounting plate such that the arm can be displaced in a horizontal direction along a third axis.

2. The device of claim 1, further including:

a table portion, wherein the mounting plate of the motion component is fixedly attached to the table portion.

3. The device of claim 2, wherein the table portion includes a top, a bottom, a first side, a second side opposite the first side, a first end, and a second end opposite the first end, wherein the mounting plate of the motion component is attached to the bottom of the table portion, wherein the motion component is configured to provide movement of the head support vertically relative to the top and bottom of the table portion, wherein the motion component is configured to provide movement of the head support horizontally relative to the sides of the table portion, and wherein the motion component is configured to provide movement of the head support horizontally relative to the ends of the table portion.

4. The device of claim 3, wherein the motion component is configured to provide movement of the head support vertically relative to the top and bottom of the table portion through a range of motion up to 130 degrees, wherein the motion component is configured to provide movement of the head support horizontally relative to the sides of the table portion through a range of motion up to 120 degrees, and wherein the motion component is configured to provide movement of the head support horizontally relative to the ends of the table portion through a range of motion up to 6 inches.

5. The device of claim 1, wherein the motion component is configured to provide rotational movement of the head support about the first longitudinal axis of the arm.

6. The device of claim 5, wherein the motion component is configured to provide rotational movement of the head support about the first longitudinal axis of the arm through a range of motion up to 90 degrees.

7. The device of claim 3, wherein the motion component is configured to provide pivotal movement of the head support on the arm relative to the ends of the table portion.

8. The device of claim 7, wherein the motion component is configured to provide pivotal movement of the head support on the arm relative to the ends of the table portion through a range of motion up to 60 degrees.

9. The device of claim 1, further including a brace configured to secure a patient's head to the head support.

10. A cervical vertebrae treatment device including:

a head support configured to support a patient's head; and a motion component operably connected to the head support, wherein the motion component comprises:

a mounting plate;

an arm support rotatably connected to the mounting plate;

an arm operably connected to the arm support and the head support;

a first motor mounted to the arm support and configured to rotate the arm with respect to the arm support about a longitudinal axis of the arm;

a second motor operably connected to the arm support and the mounting plate to rotate the arm support and the arm to cause displacement of the arm along a first linear axis; and a third motor operably connected to the arm support and the mounting plate and configured to rotate the arm support and the arm to cause displacement of the arm along a second linear axis;

wherein the first linear axis and the second linear axis are orthogonal to each other.

11. The device of claim 10, further including a control system operably connected to the motion component, wherein the control system is configured to control operation of the first motor, the second motor, and the third motor of the motion component.

12. The device of claim 11, wherein the control system includes a switch configured to deactivate the motion component, and wherein the switch is at least one of voice activated and manually activated.

13. The device of claim 11, wherein the control system includes:

a user interface configured to allow at least one of patient information and treatment information to be input; and a computer processor operably connected to the user interface, wherein the computer processor is configured to control operation of the motion component based on at least one of the patient information and the treatment information.

14. The device of claim 13, wherein the user interface is configured to allow input of treatment information that comprises exercise type, and wherein exercise type includes at least one of: vertical flexion, lateral flexion, extension, circumduction, sacro-occipital motion and head support rotation.

15. The device of claim 13, wherein the user interface is configured to allow input of treatment information that includes at least one of: number of repetitions of an exercise, range of motion of an exercise, speed of an exercise, and torque implemented in an exercise.

16. The device of claim 15, wherein the user interface is configured to allow input of treatment information that includes at least one of: an indication as to whether the speed of an exercise is constant or not constant, and an indication as to whether the torque implemented in an exercise is constant or not constant.

17. The device of claim 13, wherein the control system further includes a database operably connected to the user interface and the computer processor, wherein the database contains at least one of historical patient information and historical treatment information, and wherein the computer processor is configured to control operation of the motion component based on at least one of the historical patient information and the historical treatment information.

* * * * *